US010383512B2

(12) United States Patent
Lai (10) Patent No.: US 10,383,512 B2
(45) Date of Patent: Aug. 20, 2019

(54) SUBJECTIVE WAVEFRONT REFRACTION USING CONTINUOUSLY ADJUSTABLE WAVE PLATES OF ZERNIKE FUNCTION (71) Applicant: Shui T. Lai, Windermere, FL (US)

(72) Inventor: Shui T. Lai, Windermere, FL (US)

(*) Notice: Subject to any disclaimer, the term of this patent is extended or adjusted under 35 U.S.C. 154(b) by 42 days.

(21) Appl. No.: 15/137,243

(22) Filed: Apr. 25, 2016

(65) Prior Publication Data
US 2016/0310001 A1  Oct. 27, 2016

Related U.S. Application Data (60) Division of application No. 12/790,977, filed on May 31, 2010, now Pat. No. 9,320,426, which is a division
(Continued)

(51) Int. Cl.
*A61B 3/02* (2006.01)
*A61B 3/036* (2006.01)
*G02C 7/02* (2006.01)
*A61B 3/00* (2006.01)
*A61B 3/032* (2006.01)

(52) U.S. Cl.
CPC ............ *A61B 3/036* (2013.01); *A61B 3/0008* (2013.01); *A61B 3/0025* (2013.01); *A61B 3/032* (2013.01); *G02C 7/02* (2013.01)

(58) Field of Classification Search
USPC ........ 351/200, 205, 206, 209–211, 221, 222, 351/236, 245–246
See application file for complete search history.

(56) References Cited

U.S. PATENT DOCUMENTS 2,277,122 A  3/1942 Lowry
3,067,647 A  12/1962 Sato
(Continued)

FOREIGN PATENT DOCUMENTS

EP  1630602 A2  3/2006
EP  1625425 B1  1/2007
(Continued)

OTHER PUBLICATIONS

PCT International Preliminary Report on Patentability (Chapter II of the Patent Cooperation Treaty), for PCT Application No. PCT/US2007/062165, dated Nov. 6, 2008, 16 pages.
(Continued)

*Primary Examiner* — Brandi N Thomas
(74) *Attorney, Agent, or Firm* — SF Bay Area Patents, LLC; Andrew V. Smith (57) ABSTRACT A wavefront device produces adjustable amplitudes in optical path differences and adjustable axis orientation angles. two substantially identical wave plates have a wavefront profile of at least the third order Zernike polynomial function which are not circularly symmetric, as denoted by Z(i,j) where $i \geq 3$ and $j \neq 0$. The wave plates are mounted in rotatable mounts with their optical centers substantially aligned with each other. An subjective wavefront refraction instrument and method are provided to correct low and high order aberrations of the eye, using the adjustable wave plates that have astigmatism and higher order Zernike function optical path difference wavefront profiles.

24 Claims, 6 Drawing Sheets

Related U.S. Application Data of application No. 11/746,051, filed on May 8, 2007, now Pat. No. 7,726,811, and a continuation-in-part of application No. 11/675,079, filed on Feb. 14, 2007, now Pat. No. 7,699,471.

(60) Provisional application No. 60/746,772, filed on May 8, 2006, provisional application No. 60/773,758, filed on Feb. 14, 2006.

(56) References Cited

U.S. PATENT DOCUMENTS

| | | |
|---|---|---|
| 3,634,003 A | 1/1972 | Guyton |
| 3,639,042 A | 2/1972 | Grolman |
| 3,664,631 A | 5/1972 | Guyton |
| 3,669,530 A | 6/1972 | Guyton |
| 3,718,386 A | 2/1973 | Lynn et al. |
| 3,822,932 A | 7/1974 | Humphrey |
| 3,874,774 A | 4/1975 | Humphrey |
| 3,905,688 A | 9/1975 | Decker et al. |
| 3,927,933 A | 12/1975 | Humphrey |
| 3,936,163 A | 2/1976 | Toth |
| 3,944,347 A | 3/1976 | Barkdoll et al. |
| 3,947,097 A | 3/1976 | Humphrey |
| 3,969,020 A | 7/1976 | Lynn et al. |
| 3,973,837 A | 8/1976 | Page |
| 4,015,899 A | 4/1977 | Humphrey |
| 4,070,115 A | 1/1978 | Humphrey |
| 4,105,302 A | 8/1978 | Tate, Jr. |
| 4,105,303 A | 8/1978 | Guyton |
| 4,113,363 A | 9/1978 | Humphrey |
| 4,166,255 A | 8/1979 | Graham |
| 4,192,582 A | 3/1980 | Aoki et al. |
| 4,385,813 A | 5/1983 | Klein et al. |
| 4,395,097 A | 7/1983 | Mohrman |
| 4,396,258 A | 8/1983 | Hazard |
| 4,407,571 A | 10/1983 | August et al. |
| 4,426,140 A | 1/1984 | Stephens |
| 4,465,348 A | 8/1984 | Lang et al. |
| 4,679,921 A | 7/1987 | Yamada |
| 5,420,651 A | 5/1995 | Kamppeter |
| 5,434,630 A | 7/1995 | Bransome |
| 5,512,965 A * | 4/1996 | Snook .......... A61B 3/1005 351/205 |
| 5,549,632 A | 8/1996 | Lai |
| 5,596,378 A | 1/1997 | Kelman |
| 5,617,157 A | 4/1997 | Shalon et al. |
| 5,662,706 A | 9/1997 | Legerton et al. |
| 5,844,660 A | 12/1998 | Uchida et al. |
| 5,895,422 A | 4/1999 | Hauber |
| 5,984,916 A | 11/1999 | Lai |
| 5,993,438 A | 11/1999 | Juhasz et al. |
| 6,033,740 A | 3/2000 | Oelbrandt et al. |
| 6,048,064 A * | 4/2000 | Hosoi .......... A61B 3/0025 351/212 |
| 6,050,687 A | 4/2000 | Bille et al. |
| 6,126,731 A | 10/2000 | Kemeny et al. |
| 6,149,272 A | 11/2000 | Bergner et al. |
| 6,155,684 A | 12/2000 | Bille et al. |
| 6,210,401 B1 | 4/2001 | Lai |
| 6,325,513 B1 | 12/2001 | Bergner et al. |
| 6,325,792 B1 | 12/2001 | Swinger et al. |
| 6,450,642 B1 | 9/2002 | Jethmalani et al. |
| 6,511,180 B2 | 1/2003 | Guirao et al. |
| 6,527,716 B1 | 3/2003 | Eppstein |
| 6,676,653 B2 | 1/2004 | Juhasz et al. |
| 6,682,195 B2 | 1/2004 | Dreher |
| 6,706,036 B2 | 3/2004 | Lai |
| 6,712,466 B2 | 3/2004 | Dreher |
| 6,746,121 B2 | 6/2004 | Ross et al. |
| 6,761,453 B2 | 7/2004 | Wilson |
| 6,761,454 B2 * | 7/2004 | Lai .......... A61B 3/1015 351/216 |
| 6,781,681 B2 | 8/2004 | Horwitz |
| 6,813,082 B2 | 11/2004 | Bruns |
| 6,836,371 B2 | 12/2004 | Lai et al. |
| 6,840,619 B2 | 1/2005 | Dreher |
| 6,934,088 B2 | 8/2005 | Lai et al. |
| 6,942,339 B2 | 9/2005 | Dreher |
| 6,976,641 B2 | 12/2005 | Lai et al. |
| 6,989,008 B2 | 1/2006 | Payman |
| 6,989,938 B2 | 1/2006 | Bruns |
| 7,021,764 B2 | 4/2006 | Dreher |
| 7,034,949 B2 | 4/2006 | Horwitz |
| 7,114,808 B2 | 10/2006 | Lai et al. |
| 7,188,950 B2 | 3/2007 | Dreher et al. |
| 7,216,984 B2 | 5/2007 | Hosoi |
| 7,217,375 B2 | 5/2007 | Lai |
| 7,220,255 B2 | 5/2007 | Lai |
| 7,234,810 B2 | 6/2007 | Warden et al. |
| 7,246,906 B2 | 7/2007 | Mihashi et al. |
| 7,249,847 B2 | 7/2007 | Dreher |
| 7,286,295 B1 | 10/2007 | Sweatt et al. |
| 7,329,001 B2 | 2/2008 | Bernashid et al. |
| 7,699,471 B2 | 4/2010 | Lai |
| 7,726,811 B2 | 6/2010 | Lai |
| 8,366,274 B2 | 2/2013 | Lai |
| 2002/0140902 A1 | 10/2002 | Guirao et al. |
| 2003/0003295 A1 | 1/2003 | Dreher et al. |
| 2003/0013339 A1 | 1/2003 | Pan |
| 2003/0053027 A1 | 3/2003 | Sarver |
| 2003/0053031 A1 | 3/2003 | Wirth |
| 2003/0095889 A1 | 5/2003 | Gottuso |
| 2003/0143391 A1 | 7/2003 | Lai |
| 2004/0100619 A1 | 5/2004 | Olivier et al. |
| 2004/0160576 A1 | 8/2004 | Lai et al. |
| 2004/0189935 A1 | 9/2004 | Warden et al. |
| 2004/0235974 A1 | 11/2004 | Lai |
| 2004/0243112 A1 | 12/2004 | Bendett et al. |
| 2004/0267283 A1 | 12/2004 | Mavor et al. |
| 2005/0046957 A1 | 3/2005 | Lai et al. |
| 2005/0104240 A1 | 5/2005 | Jethmalani et al. |
| 2005/0105044 A1 | 5/2005 | Warden et al. |
| 2005/0174535 A1 | 8/2005 | Lai et al. |
| 2005/0200809 A1 | 9/2005 | Dreher et al. |
| 2005/0225725 A1 | 10/2005 | Warden et al. |
| 2005/0259221 A1 | 11/2005 | Marmo |
| 2005/0260388 A1 | 11/2005 | Lai |
| 2006/0007397 A1 | 1/2006 | Lai |
| 2006/0017990 A1 | 1/2006 | Platt et al. |
| 2006/0050228 A1 | 3/2006 | Lai et al. |
| 2006/0052547 A1 | 3/2006 | Jethmalani et al. |
| 2006/0119792 A1 | 6/2006 | Dreher |
| 2006/0181677 A1* | 8/2006 | Schmid .......... A61F 9/00 351/206 |
| 2007/0153232 A1 | 7/2007 | Warden et al. |
| 2007/0195264 A1 | 8/2007 | Lai |
| 2007/0208363 A1 | 9/2007 | Lai |
| 2007/0258046 A1 | 11/2007 | Lai |
| 2007/0291224 A1 | 12/2007 | Lai |
| 2008/0037135 A1 | 2/2008 | Lai |
| 2008/0039825 A1 | 2/2008 | Lai |
| 2008/0212024 A1 | 9/2008 | Lai |

FOREIGN PATENT DOCUMENTS

| | | |
|---|---|---|
| EP | 1439946 B1 | 4/2007 |
| EP | 1535104 B1 | 4/2007 |
| EP | 2026693 A4 | 1/2010 |
| EP | 2020904 B1 | 3/2012 |
| EP | 2468174 A1 | 6/2012 |
| EP | 2520220 A1 | 11/2012 |
| WO | 98/27863 A1 | 7/1998 |
| WO | 02/38092 A1 | 5/2002 |
| WO | 03/034909 A2 | 5/2003 |
| WO | 2004/096014 A2 | 11/2004 |
| WO | 2005/038015 A1 | 4/2005 |
| WO | 2005/062818 A2 | 7/2005 |
| WO | 2005/079546 A2 | 9/2005 |
| WO | 2006/020605 A2 | 2/2006 |
| WO | 2007/044967 A2 | 4/2007 |
| WO | 2007/095596 A2 | 8/2007 |
| WO | 2007/044967 A3 | 9/2007 |
| WO | 2007/103890 A2 | 9/2007 |

(56) References Cited

FOREIGN PATENT DOCUMENTS

| WO | 2007/147152 A2 | 12/2007 |
|---|---|---|
| WO | 2007/095596 A3 | 1/2008 |
| WO | 2008/014330 A2 | 1/2008 |
| WO | 2008/014330 A3 | 2/2008 |
| WO | 2008/088571 A2 | 7/2008 |
| WO | 2007/147152 A3 | 8/2008 |
| WO | 2008/088571 A3 | 9/2008 |

OTHER PUBLICATIONS

Antonio Guirao, Ph.D. and David R. Williams, Ph.D., A Method to Predict Refractive Errors from Wave Aberration Data, Optometry and Vision Science, vol. 80, No. 1, 2003, pp. 36-42.
Jason D. Marsack, Larry N. Thibos, and Raymond A. Applegate, Metrics of optical quality derived from wave aberrations predict visual performance, Journal of Vision, vol. 4, 2004, pp. 322-328.
Xu Cheng, Arthur Bradley, and Larry N. Thibos, Predicting subjective judgment of best focus with objective image quality metrics, Journal of Vision, vol. 4, 2004, pp. 310-321.
Internet printout: TISSEEL VH [Fibrin Sealant], Retrieved from URL: http://www.baxter.com/products/biopharmaceuticals/biosurgery/sub/tisseel.html.
TISSEEL VH [Fibrin Sealant] product information, Retrieved from URL: http://www.baxter.com/products/biopharmaceuticals/downloads/Tisseel_PI.pdf.
Laser in situ Keratomileusis (LASIK), Retrieved from URL: http://www.surgeryencyclopedia.com/La-Pa/Laser-In-Situ-Keratomileusis-LASIK.html.
Laser Epitheial Keratomileusis (LASEK), Retrieved from URL: http://en.wikipedia.org/wiki/Photorefractive_keratectomy.
Conductive Kerotoplasty (CK), Retrieved from URL: http://www.allaboutvision.com/visionsurgery/ck/ltk_eye_surgery.htm.
PCT Notification Concerning Transmittal of International Preliminary Report on Patentability (Chapter I of the Patent Cooperation Treaty), for PCT Application No. PCT/US2007/068510, dated Nov. 20, 2008, 6 pages.
PCT Invitation to Pay Additional Fees and, Where Applicable, Protest Fee, for PCT Application No. PCT/US2007/068510, dated May 14, 2008, 2 pages.
PCT Notification of Transmittal of the International Search Report and the Written Opinion of the International Searching Authority, or the Declaration, for PCT Application No. PCT/US2007/068510, dated Jul. 1, 2008, 12 pages.
EPO Communication regarding the transmission of the European search report, European search opinion, Supplementary European search report, for European patent application No. 07872213.9, report dated Dec. 22, 2010, 5 pages.
EPO Communication regarding the transmission of the European search report, European search opinion, Supplementary European search report, for European patent application No. 12001804.9, report dated May 24, 2012, 11 pages.
EPO Communication regarding the transmission of the European search report, European search opinion, Supplementary European search report, for European patent application No. 12002549.9, report dated Oct. 9, 2013, 4 pages.
EPO Communication regarding the transmission of the European search report, European search opinion, Supplementary European search report, for European patent application No. 07757012.5, report dated Dec. 15, 2009, 12 pages.

* cited by examiner

SUBJECTIVE WAVEFRONT REFRACTION USING CONTINUOUSLY ADJUSTABLE WAVE PLATES OF ZERNIKE FUNCTION

PRIORITY

This application is a Divisional of U.S. patent application Ser. No. 12/790,977, filed May 31, 2010, now U.S. Pat. No. 9,320,426; which is a Divisional of U.S. patent application Ser. No. 11/746,051, filed May 8, 2007, now U.S. Pat. No. 7,726,811; which claims the benefit of priority to U.S. provisional patent application No. 60/746,772, filed May 8, 2006, and is a Continuation in Part (CIP) of U.S. patent application Ser. No. 11/675,079, filed Feb. 14, 2007, now U.S. Pat. No. 7,699,471; which claims priority to U.S. provisional patent application No. 60/773,758, filed Feb. 14, 2006.

BACKGROUND

Before the advent of the wavefront aberrometer, many patients' visual symptoms were collectively referred to as a result of "irregular astigmatism". Increasingly, more ophthalmologists and optometrists have begun measuring wavefront errors of patients' eye. A wealth of information is now available, that was not heretofore, from auto-refractor or cornea topography measurements. Use of a wavefront map as a diagnosis tool is also gaining popularity, and vision care professionals use it to explain diagnoses to patients having visual complaints.

It is useful to understand the source of a problem. However, patients are most interested in solutions; such as getting rid of visual complaints, and improving their quality of vision. Currently, laser refractive surgery, such as LASIK, is one possible solution. However, laser surgery is invasive and the tissue healing process following surgery can induce its own set of aberrations, often rendering an attempt to correct the pre-operation errors fruitless. It has been proposed to correct high order aberrations (HOA) with non-invasive devices such as spectacles or contact lenses.

It was proposed in US application 2004/0160576A1, which is hereby incorporated by reference, to identify high order wavefront errors with a patient feedback control process. However, lacking in that disclosure is the basis for a patient to adjust each of the wavefront components. The '160576 application does disclose use of visual acuity as a measure to find an end point. As it was pointed out in the '160576 application, an acuity chart, or Snellen letter chart, is not an ideal target for wavefront optimization. More importantly, no method is presented regarding how a patient may choose which Zernike function to vary among the dozens of Zernike functions, without which the patient would have to go on a random walk, using by trial and error on all or substantially all of the Zernike functions. Without a clear step by step procedure, a patient may not even be able to find an optimal sphere, cylinder and axis, much less the high order Zernike components, wherein the effect of those aberrations on acuity is much smaller. The patient might get totally lost in the process, and it might take hours to come to any final optimized combination, if it ever got there at all.

Recognized by the Inventor

Improving quality of vision is more complicated than measuring the HOA and canceling them. Higher order aberrations are typically much smaller in amplitude compared to the defocus and astigmatism terms, and they vary from eye to eye. The question arises as to whether there would be visual benefits by correcting them in some patients. Also, the brain plays a key part in interpreting and in forming perceived images of what one sees. The optical image formed at the retina is only a starting point.

If one can measure the HOA; then one can cancel them optically. However, as it was pointed out, it is not clear whether if this cancellation results in improvement in one patient, then the same approach will work for a different patient.

In embodiments described herein, tools are provided for performing a subjective method for a patient. In a preferred embodiment, not just the sphere and cylinder and axis are handled, but the HOA errors are refracted as well. That is, using a technique in accordance with a preferred embodiment, a patient can actually see through a combination of wave plates that are adjustable in amplitude, and preferably also in angle. With this technique, a patient can actually see whether a wavefront correction, as presented to the patient, provides any benefits. A subjective technique in accordance with a preferred embodiment stands in contrast with objective techniques in which HOA errors of an eye are measured and a spectacle or contact lens is provided to cancel the HOA, and wherein the patient finds out only later if the device offers any benefits at all when he or she receives the corrective device.

In a preferred embodiment, an instrument is provided that comprises wave plates of Zernike functions, each of which is continuously adjustable in amplitude, and preferably also in angle. In addition, a continuously variable wave plate assembly is alternatively provided for utilizing a series of wave plates in small increment steps. These wave plates can be arranged on a disk, like a series of lenses in a phoropter, and the system can be made affordable for most eye care professionals.

SUMMARY OF THE INVENTION

A wavefront device that produces adjustable amplitudes in optical path differences and adjustable axis orientation angles is provided. Two substantially identical wave plates have a wavefront profile of at least the third order Zernike polynomial functions which are not circularly symmetric, as denoted by $Z(i,j)$ where $i \geq 3$ and $j \neq 0$. The wave plates are mounted in rotatable mounts with their optical centers substantially aligned with each other.

The device may include a pinion gear engaging with bevel gears including at least one bevel gear attached to each of the rotatable mounts, wherein rotating the pinion gear may cause the wave plates to rotate in opposite direction at a substantially equal angular rate to cause a change in amplitude of the device. Electric motors with drive mechanisms may drive the wave plates at a same angular rate substantially in synchronization, while the wave plates move in equal amount and in opposite direction to change a wavefront amplitude. The wave plates are moved in a same direction to change an optic axis angle direction.

A method of generating a subjective optical prescription with a Zernike wave plate having an ability to substantially continuously adjust its amplitude and optic axis angle is also provided. Two substantially identical wave plates have a wavefront profile of a Zernike polynomial function. Optical centers of the wave plates are aligned. The wave plates are rotated in opposite direction in one or more substantially identical angular amounts until a patient indicates an optimal setting. The entire assembly is rotated including the two wave plates to an optic axis angle indicated as optimal by the patient. An optical prescription is generated based on initial positions and rotation amounts of the two wave plates. The rotating of the two wave plates may include rotating a pinion gear which engages with bevel gears that are mounted with the wave plates.

A method of determining second order and higher order aberrations of a patient's eye is also provided. Zernike functions are provided in a predetermined order in a priority list. At least one point source is provided as a viewing target. A first adjustable wave plate is selected according to the order in the priority list. The first adjustable wave plate is placed in a patient's line of sight. A refractive error of the patient is minimized by adjusting amplitude and angle of the first adjustable wave plate while the patient is looking at the viewing target. These are repeated for one or more further wave plates according to the order in the priority list, until no appreciable further improvement in image quality of the point source is observed by the patient.

The priority list may include $Z(2,0)$, $Z(2,+/-2)$, and $Z(3, +/-1)$, in that order, and may further include $Z(3+/-3)$ after $Z(3, +/-1)$, and may further include $Z(4,+/-2)$, $Z(5,+/-1)$, $Z(4,+/-4)$, $Z(5,+/-3)$, $Z(6,+/-2)$, $Z(6,+/-4)$, $Z(5,+/-5)$, in that order, after $Z(3+/-3)$. The placing of the first adjustable wave plate may include positioning the first wave plate of the Zernike function at a conjugate corneal or pupil plane of the patient.

Refractive errors of third or higher order Zernike function aberrations may also be minimized. An input device is provided to the patient. An optic axis angle of an adjustable wave plate of third or higher order Zernike profile which is disposed at a conjugate corneal or pupil plane of the patient is varied while the patient is looking at the viewing target. An amplitude of the adjustable wave plate of third or higher order is varied also while the patient is looking at the viewing target. An indication is received from a patient that a predetermined end point has been reached by activation of the input device, The method may also include varying the angle of the wave plate of third or higher order, finding an optimal angle position, and then varying the amplitude of the adjustable wave plate. The predetermined end point may include a sharpest image of the point source target as indicated by the patient.

Contact or intraocular lenses may be provided and/or an ablation profile of refractive surgery may be determined such as for LASIK, PRK, LASEK, and/or intra-corneal surgery.

A method of correcting refractive errors of second and higher order aberrations of an eye is also provided. Second order aberrations are determined using adjustable $Z(2,0)$ and $Z(2,+/2)$ Zernike wave plates. Higher orders aberrations are corrected using $Z(2,0)$ and higher Zernike terms, wherein $Z(2,0)$ substantially corrects aberrations of all higher order Zernike terms that are spherically symmetric.

A further device for determining or correcting aberrations of an eye is also provided. The device includes at least one adjustable wave plate having adjustable amplitude and optic axis angle. A priority list of Zernike functions is provided such that adjustable wave plates may be selected in accordance with an order of Zernike functions in the list. A point source is provided as a viewing target. The one or more selected wave plates are placed at a conjugate corneal or spectacle plane of a patient's eye. A patient searches for predetermined image end points while looking at the point source while angle and amplitude of the selected wave plate are varied.

The priority list may include $Z(2,0)$, $Z(2,+/-2)$, and $Z(3, +/-1)$, in that order, and may further include $Z(3+/-3)$ after $Z(3, +/-1)$, and may further include $Z(4,+/-2)$, $Z(5,+/-1)$, $Z(4,+/-4)$, $Z(5,+/-3)$, $Z(6,+/-2)$, $Z(6,+/-4)$, $Z(5,+/-5)$, in that order, after $Z(3+/-3)$. The placing of the first adjustable wave plate may include positioning the first wave plate of the Zernike function at a conjugate corneal or pupil plane of the patient.

The ordering of the priority list may be modified according to an aberration amplitude of the patient's eye in Zernike function as determined by a subjective wavefront aberrometer. The priority list may be modified by a condition of the patient's eye, including a keratoconus and/or a corneal transplant condition. The priority list may be modified by weighting factors with relative values affecting the ordering of the list as determined by the clinical experience of a physician.

The adjustable wave plate may include adjustable wave plates $Z(2,0)$ and $Z(2,+/-2)$, and/or another wavefront device such as liquid crystal wave plates or deformable mirrors. The other wavefront device may produce adjustable amplitudes in optical path differences and adjustable axis orientation angles, and include two substantially identical wave plates with wavefront profile of at least the third order Zernike polynomial function, which are not circularly symmetric, as denoted by $Z(i,j)$ where $i \geq 3$ and $j \neq 0$. The wave plates may be mounted in rotatable mounts with their optical centers substantially aligned with each other.

The adjustable wave plate may include at least one substantially identical pair of wave plates having a Zernike function optical path difference profile, a deformable mirror and/or a liquid crystal wave plate.

An optical instrument is also provided for generating a prescription for one or more corrective lenses or corrective procedures for a patient by subjective refraction. The instrument includes a stable frame having a defocus corrector assembly (DCA) and an astigmatism corrector assembly coupled thereto. The DCA causing a change of defocus power at the patient's eye, and includes a first motor and at least two DCA lenses disposed along an optical axis between an image source and the patient's eye. At least one of the DCA lenses is movable relative to the frame along the optical axis for adjusting defocus power and/or is replaceable with one or more further lenses with incremental dioptric powers. The defocus power may be thereby measurably adjustable until the patient indicates that an initially blurry view of the image source has become substantially sharp. The ACA causes a change of astigmatism power, and includes a second motor and at least two astigmatism plates disposed along the optical axis that are relatively rotationally adjustable and/or wherein at least one of the ACA astigmatism plates is replaceable with one or more further cylindrical lenses. The astigmatism power is thereby measurably adjustable until the patient indicates that an initially elongate view of the image source has become substantially round.

The instrument may further include electrical and/or electronics hardware and/or computer programs for performing individually or collectively one or more of the following tasks:
  (i) drive movement of one or more optical elements in the DCA or ACA, or both, to change defocus or astigmatism power, or both;
  (ii) display a location of an optical element;
  (iii) convert a location or orientation reading, or both, to a refractive power in units of diopters;
  (iv) collect data relating to adjustments to the DCA and ACA;
  (v) set limits of movement range for the DCA or ACA or both to avoid over-correction;

(vi) automatically advance DCA or ACA refractive power, or both, when such task is requested; or (vii) automatic align the ACA optical axis when such task is requested, or combinations thereof.

The ACA may provide a variable astigmatism correction amplitude or variable axis angle, or both. The ACA may include a first wave plate having a second order Zernike polynomial of astigmatism wavefront correction profile in an x-y plane. A second wave plate may have a second order Zernike polynomial of astigmatism wavefront correction profile in the x-y plane. The first and the second wave plates may be mounted with their wavefront profile origins aligned along an axis (Z-axis). One or more of the wave plates may be angularly adjustable with respect to said Z-axis. The wavefront profile of the Zernike polynomial of astigmatism of the first and second wave plates may include $Z(2,2)$ or $Z(2,-2)$. Both of the wave plates may be angularly adjustable with respect to the Z-axis.

First and second ACA astigmatism plates may be mounted on first and second rotary ball bearings, and first and second bevel gears may be coupled to the first and second ball bearings. A first pinion gear may drive the first and second bevel gears for oppositely rotating the first and second ACA plates. A second motor may drive the first pinion gear. A rotary angle sensing device may be coupled to a rotary encoder. A second pinion gear may be mounted between the first and second bevel gears.

The ACA may be further for causing a change in orientation of axis angle. At least two astigmatism plates of said ACA may be rotatable together as a whole. The optical instrument may further include third and fourth ball bearings coupled to the first and second ball bearings, respectively, and to the frame. A third bevel gear may be coupled to at least one of the third and fourth ball bearings. A third motor may be for rotating the astigmatism plates of the ACA assembly together. A second rotary encoder may be coupled to a fourth pinion gear for sensing angular rotation of the ACA assembly.

The instrument may include an optics holder for each of the DCA lenses. A linear slide may be coupled to the optics holder of at least one of the DCA lenses. A motor and lead screw may move the linear slide.

A computer program product may include a processor and a computer program for calculating amplitudes of the ACA plates from relative and/or absolute angular movement and/or for calculating diopter power of the DCA. Readable results may be output. The computer program product may also form an ordered list of decreasing significance of Zernike functions based on RMS amplitude of a patient's measured wavefront errors. The computer program product may also control measurements according to the ordered list. Measurements for Zernike functions having a RMS amplitude less than 0.05 may be omitted. The ordered list may include second order Zernike function, Coma, Trefoil and secondary astigmatism.

The optical instrument may further include an input device for the patient or for an examination administrator or both. The image source may include a plane wave light source including substantially a point light source as a viewing target. A quality vision marker (QVM) may include one or more display items including one or more lines, one or more circles, one or more points disposed along a pattern of one or more lines or circles, or combinations thereof. The marker may provide a display pattern including one or more rings and/or parallel lines. A reference marker may provide a sweep line overlapping at the image source and having an orientation which is adjustable using the at least one input device until the patient indicates that the sweep line is aligned with a sharper linear image of the image source. Axis angle data of astigmatism errors of the patient's eye may be thereby provided.

The image source may include a plane wave point source placed two meters or farther away from the patient and having a diameter of two millimeters or less, or a substantially collimated light beam from a laser source that simulates a point source positioned two meters or farther away from the patient. An additional lens may be disposed to cause the image source to appear to the patient to be two meters or farther away. Spectral contents of the image source may include white light, substantially blue light, substantially yellow light, or substantially red light.

One or more spectacle, contact or intraocular lenses may have a prescription based on measurements by the optical instrument described herein.

DETAILED DESCRIPTION OF PREFERRED AND ALTERNATIVE EMBODIMENTS

In the entire specification, the term "wavefront refraction" shall be broadly construed to include any process of providing wavefront compensation to a patient's eye, while the patient is looking at a target. A "wavefront refractor" is a device which an eye care professional may use to perform refraction that includes correcting higher order aberrations of the eye, or sometimes referred to as higher order refractive errors. The "+/−" is also used herein before the second index of Zernike functions to represent a grouping of the pair of Zernike polynomials that have a same first index, wherein the second index has opposite sign. For example, the pair of Trefoil, $Z(3,-3)$ and $Z(3,3)$ are to be paired, and $Z(3,+/-3)$ shall designate a combination of the two Trefoils in an adjustable wave plate configuration. The term wave plate shall mean an optical plate that has the property of inducing an optical path difference profile. When a light wave passes the plate, the spatial profile across the two dimensions of the plate surface has a change in its wavefront in accordance with the optical path difference profile. A Zernike wave plate shall mean the optical path difference has a cross sectional profile as that of a Zernike function profile. The optical axis of a Zernike function may be assigned in accordance with a major symmetry axis of the Zernike function. For example the optical axis of $Z(2,+/-2)$ can be chosen either at zero degree or 90 degrees, and in this case selected according to an assignment of cylindrical cylinder lens axis.

Construction of Continuously Adjustable Zernike Function Wave Plates

The Zernike function wave plates described in the following can be manufactured using high precision free form diamond turning CNC machine, which is commercially available from Schneider, Germany. We adapt the Optical Society of America (OSA) convention for the Zernike functions, but omit the normalization constant for convenience. Using the trefoils as an example, and adding an amplitude and angular notation in the Zernike function designation. Two Zernike functions of Trefoil both having an amplitude of unity, and at an angle θ, are expressed as:

$$Z(3,-3,1,\theta)=\rho^3 \sin(3\theta)$$

$$Z(3,+3,1,\theta)=\rho^3 \cos(3\theta)$$

Note that: $Z(3,-3, 1, \theta)=Z(3,+3, 1, \theta+90/3)$, namely, the two trefoils in the Zernike polynomial functions are in fact identical except for an angular offset of 30 degrees.

Suppose that one desires to have a variable wave plate of trefoil with variable amplitude ranging from 0 to 5. One first fabricates two identical Trefoil wave plates each with an amplitude of 2.5:

$$Z(3,-3,2.5,\theta)=2.5\rho^3 \sin(3\theta).$$

One achieves a total cancellation if one rotates one trefoil in the pair by 30 degrees relative to the second trefoil.

$$Z(3,-3,2.5,\theta+30)=2.5\rho^3 \sin(3(\theta+30))=-2.5\rho^3 \sin(3\theta)$$

$$Z(3,-3,2.5,\theta)+Z(3,-3,2.5,\theta+30)=Z(3,-3,2.5,\theta)-Z(3,+3,2.5,\theta)=0$$

When two identical Trefoils are aligned:

$$Z(3,-3,2.5,\theta)+Z(3,-3,2.5,\theta)=Z(3,-3,5,\theta).$$

Now, one can vary the Trefoil pair to any amplitude value, between 0 and 5, by rotating one or the other. It is preferable to rotate the pair simultaneously in identical angle, or approximately, but in opposite direction. That way, the optical axis of the combined wave plate assembly remains stationary, while the amplitude is adjusted.

The sum amplitude of 5 from a pair of plates with amplitude of 2.5 is used merely as an example for illustration. No limitation is to be inferred on the range of the amplitude of the Zernike wave plate assembly using a technique in accordance with a preferred embodiment.

Likewise, one can construct continuously adjustable Coma wave plates by substantially following the above steps, except replacing the Zernike function designation from a Trefoil to a Coma designation, basically by replacing the second index +/−3, inside the bracket, with +/−1.

For the fourth order Zernike terms, like tetrafoils $Z(4,+/-4, 1, \theta)$, the method described above also applies. In this case, the continuously adjustable device comprises two tetrafoil wave plates of equal amplitude. However, the total cancellation, or the zero tetrafoil, occurs when the relative angle θ is at 90/4, or 22.5 degrees. Moreover, the technique of this preferred embodiment may also be used to construct continuously adjustable secondary-tetrafoils $Z(4,+/-2, 1, 0)$, because the angular part of the secondary-tetrafoil is identical to the those of tetrafoils.

Zernike functions other than those with a zero in the second index, such as $Z(4,0)$, $Z(6,0)$, etc., can be paired off (those terms that have almost identical designation, except for a plus/minus sign difference in the second index in their functional representation), and a continuously adjustable device can be constructed using the technique provided above.

The Visual Significance of Symmetric Zernike Functions and their Correction

Concerning the Zernike terms of fourth order and higher, and having a second index of zero, the following three points are noted. First, these terms are symmetric in nature, while irregularly shaped corneas that cause serious visual symptoms and complaints such as keratoconus are seldom rotationally symmetric. Second, the point spread function resulting from these aberration terms have a tight focus, but with some halo effect at nighttime around bright light sources. The visual acuity is not so affected during daytime, but the contrast sensitivity would suffer to some extent. Third, and fortunately, the defocus term $Z(2,0)$ can be used effectively to counteract these aberrations, canceling most, if not all, of the aberration from these fourth order and higher Zernike terms. Therefore, the compromise on the quality of vision may be made small and even negligible by not having a continuously adjustable symmetric wave plate for $Z(4,0)$, $Z(6,0)$ and those of even higher order terms.

Subjective Wavefront Refractor Having Continuously Adjustable Zernike Function Wave Plates Previously, the same inventor has filed patent applications entitled, "Subjective wavefront refraction correcting low and high order aberrations", corresponding to U.S. application Ser. Nos. 60/773,758 and 11/675,079, which are incorporated by reference in their entirety.

In these referenced applications, a subjective refraction device is described, which comprises two continuously adjustable assemblies, one for the defocus $Z(2,0)$, and one for astigmatism $Z(2, +/-2)$. Using the device and method according to the referenced applications, the second order terms correct a good portion of the high order aberrations. However, there will be residual HOA.

High Order Zernike Wave Plates in a Wavefront Refractor

Figure 1A:
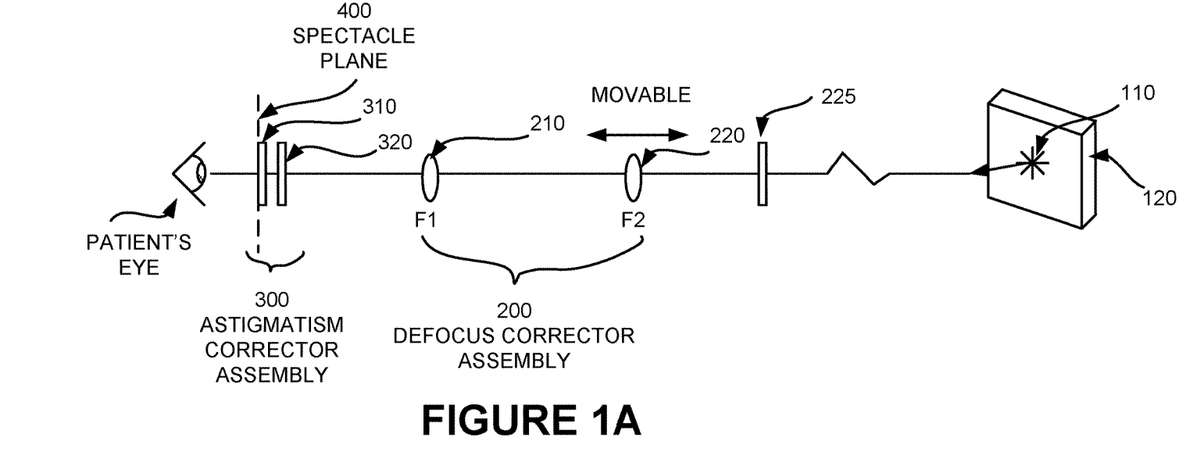
FIG. 1A illustrates subjective refraction apparatus in accordance with an embodiment.
Figure 1B:
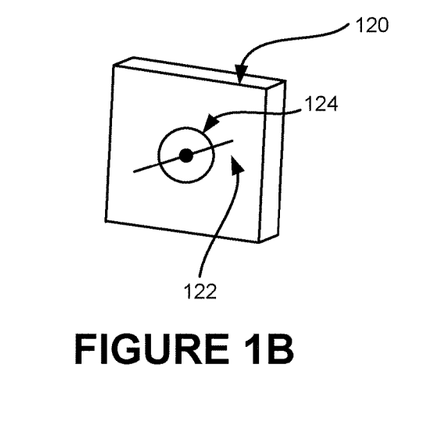
FIG. 1B illustrates a quality vision marker (QVM) including point light source in accordance with an embodiment.

Instead of positioning the Zernike wave plates right next to the patient's eye, which would be crowded, the wave plates may be advantageously positioned in accordance with another embodiment at the equivalent pupil plane (refer to FIG. 1, element 225 is a plane where the wave plates are located) after the Defocus Corrector Assembly 200, or DCA 200 in FIG. 1. FIG. 1(a) of U.S. application Ser. No. 60/773,758 is incorporated into the present specification as FIG. 1 for illustration. A wave plate can be any of a variety of optical devices that have a distribution of optical path differences across their transverse extent relative to the optical path within which they are positioned. A lens and a curved mirror are examples. A lens may be rotationally symmetric, but in the case of a trefoil, e.g., it is not. A wave plate is any reflective or transmissive optic corresponding to a selected Zernike function. For example, another wave plate is a coma wave plate. A wave plate assembly in accordance with a preferred embodiment includes at least two wave plates that can be relatively displaced to change optical amplitude or angle or both.

FIG. 1 schematically illustrates the optical layout of a device in accordance with a preferred embodiment. A conjugate pupil plane 225 of the patient's eye under examination is located at approximately the focal point 225 of the lens f2, 220 in FIG. 1, between the lens f2 220 and the target 110. The target is located ideally for positioning a pupil limiting aperture or pinhole as discussed in the referenced application. Preferably, the wave plate assembly that is located at plane 225 is also mounted on a same movable platform as the lens f2 (220) is mounted on. Thereby, the distance between lens f2 (220) and the wave plate assembly that is located at plane 225 remains the same when lens f2 (220) is moved to provide an adjustable defocus diopter power.

Processes which Utilize the Wavefront Refractor

Overcoming the Patient Selection Problem of Objective Wavefront Refraction Methods One drawback of the objective method of refracting a patient is the lack of patient feedback. Until now, commercial wavefront aberrators have been limited to measuring optical aberrations of the eye. Some have attempted to correct aberration by canceling it by way of incorporating an exact opposite of the wavefront error profile in spectacles or contact lenses. Ideally, if all the optics are aligned properly, the resulting image that forms at the retina of the patient would be diffraction limited. One remaining issue is that the patient may not appreciate the difference of the high order wavefront corrected image compared to that corrected with the second order, namely, sphere, cylinder and axis.

Therefore in accordance with certain embodiments, a measured total order wavefront error is input into the wavefront refractor. Communicating with the wavefront refractor is a computer running a computer program coupled to control the drive mechanism. The computer is preferably used to control the movement of the optical components including the defocus corrector assembly 200 including lens f1 (210) and lens f2 (220), the astigmatism assembly 300 including optics 310 and 320 shown at the spectacle plane 400 in FIG. 1, and the high order Zernike function wave plates located at plane 225 in FIG. 1, setting them to cancel the patient's wavefront error. Now, the patient looks through correction optics, including the low order optics 200, 300, and the high order wave plates at location 225, and looks at a viewing target such as a nearly collimated light beam, a small point source, real physical objects, a high definition image from a monitor, or an image from film, or a combination thereof. The patient can then decide if the high order correction does make a difference, and make a decision on the purchase of just regular eyeglasses or contact lenses, or instead pay a premium for a wavefront corrected device in accordance with a preferred embodiment. A device in accordance with a preferred embodiment eliminates uncertainty involved in "patient selection". Without the subject patient participation, objective wavefront refraction inherently involves a prior patient selection algorithm. Since no algorithm can reliably read a patient's mind, such would quite likely select the wrong candidate from time to time, with negative consequences involving patient complaints and demands for a refund of the purchase amount.

Subjective Wavefront Refraction with Patient Participation

In another embodiment, a patient subjectively adjusts wave plates, e.g., located at plane 225 in FIG. 1, to achieve optimized vision. One may use a device in accordance with a preferred embodiment to generate an HOA wavefront by selecting a combination of the Zernike function wave plates, in selected amplitudes and angles. In addition, the wave plates may comprise substantially all Zernike functions, while the patient's vision is being tested. Also, the patient can now subjectively determine an improvement in vision quality by adding/subtracting a Zernike function wave plate, and/or changing the amplitude and the angle of a Zernike function.

Forming an Ordered List of Decreasing Significance of Zernike Functions

It is recognized by the present inventor that there is great significance in establishing a procedure that leads to a final refraction point.

In one embodiment, a list is established for Zernike functions in an order of decreasing significance, and uses this ordered list to guide the patient to find the end point of subjective wavefront refraction. Here, the Zernike functions are paired with the same first index, and the second index has the numeral except in opposite sign. Trefoils may be used as an example. It was shown above that the two trefoils are in fact identical in profile except for a relative rotation of 30 degrees. Henceforth, +/− notation is used in the second index of a Zernike function to denote pairing of two Trefoil functions.

$$Z(3,+/-3,a,\varphi)=Z(3,-3,b,\theta)+Z(3,+3,c,\theta),$$

where "a" represents the resulting amplitude after combining the two trefoils with amplitude "b" and "c", and the angle $\varphi$ is the angle of orientation of the optical axis of the resulting trefoil.

In one embodiment, defocus Z(2,0) is given the top position in the ordered list, followed by astigmatism (amplitude and angle). In the following, an exemplary ordered list of Zernike functions is provided in the OSA designation, and/or a modified OSA designation with the Zernike pairing schemes as proposed in an earlier paragraph:

1. Z(2,0)
2. Z(2,+/−2)
3. Z(3,+/−1)
4. Z(3,+/−3)
5. Z(4,+/−2)
6. Z(5,+/−1)
7. Z(4,+/−4)
8. Z(5,+/−3)
9. Z(6,+/−2)
10. Z(6,+/−4)
11. Z(5,+/−5)
12. . . . .

The amplitude distribution of Zernike functions in normal human eyes drops rapidly after the fourth order terms (OSA), and second order terms are ordinarily the most prominent. The ordered list above may continue with more terms. However, the contribution of the remaining terms is expected to be small, except in cases of keratoconus eyes and those after corneal transplant surgery or traumatization, or the like. The exact ordering of the Zernike components in the list is not a limitation to the invention or embodiments thereof. In another embodiment, the placement of terms of the Zernike function in the ordered list is modified according to clinical experience learned from patient feedback when the method is used in clinical practice over time. Thereafter, a modified ordered list is to be established, or customized for a particular situation with the patient, whether the eye has keratoconus conditions or post corneal transplant.

In another embodiment, if a patient's wavefront error has been measured with a subjective wavefront aberrometer, it would be clear that certain Zernike terms are more dominant and some Zernike terms such as coma or trefoil are small or missing altogether. The small Zernike terms, with RMS amplitude of less than 0.03 microns can be skipped over from the ordered list, during the subjective wavefront refraction process. In another embodiment, the Zernike function is ordered in accordance with the RMS amplitude of the patient's wavefront errors, and the most dominant Zernike term gets moved up the list, and is followed by the next highest amplitude term, and so on.

Subjective Wavefront Refraction Procedure

In the previous U.S. application Ser. Nos. 60/773,758 and 11/675,079, detailed procedures have been given to achieve optimized values for low order Zernike terms, $Z(2,0)$ and $Z(2,+/-2)$, traditionally called the defocus and astigmatism and axis angle. In the optimization process, the refractive errors relating to defocus and astigmatism is substantially reduced. One advantageous aspect of this refraction method is in each element of the process, there is a distinct end point for the patient to search for. Therefore, each element may be achieved without confusion. What follows are exemplary end points for arriving at optimal prescriptions for eyeglasses, or contact lenses. The prescription may also be used for refractive surgery. Distinct end points may include:
1. Without correction, a patient would typically see a diffuse image of a point source viewing target. First, defocus refractive error is substantially removed by continuously adding or subtracting refractive power using the DCA device, until a relative sharp line image, or an otherwise elongated image, is formed from the point source target.
2. To correct for the astigmatism, the ACA device is adjusted to turn the line, or elongated image, and/or condense it into a substantially round image.
3. Next, the defocus power is increased or decreased, depending on whether the refraction is for a positive or negative cylinder convention, and the round image is condensed into substantially a point image.
4. For correction of a higher order aberration, greater than the second order Zernike aberrations, one attempt to reduce star bursts around a point image may be achieved in (3) above. The defocus and astigmatism may be further adjusted. Moreover, adjustments may be added with other higher order wave plates such as coma and trefoil. Third and higher order Zernike function wave plates may be used to further tighten the point image into a sharp point substantially free of star bursts.

In certain embodiments, one Zernike wave plate assembly is tested at a time. A point source, or multiple point sources as described in 60/773,758 and Ser. No. 11/675,079, may be presented to the patient as the viewing target. As in the previous disclosure, the points, or substantially the points may be arranged in a certain predetermined pattern to facilitate and improve test speed and accuracy. In testing a wave plate of third order or higher in Zernike function, the end point to be searched by a patient undergoing an eye examination is to achieve a sharpest focused point image of the point or points at the viewing target.

In accordance with an embodiment, after the low order Zernike terms have been determined, one selects the next Zernike function term from an ordered list. The list illustrated above under the heading, "Forming an Ordered List of Decreasing Significance of Zernike Functions", or a modified, abridged or expanded list, can then be used as a default list. Some re-arrangement may be derived from evidenced success from clinical feedbacks, as discussed. Assuming that clinical data confirms the significance ordering of Zernike functions in the list above, then as an example, and without inferring any limitation, the next most significant Zernike function can then be selected, which in this example is $Z(3,+/-1)$, known as the "Coma". One may first increase the amplitude as an example, in 0.05 micron increments, and between each incremental step, the patient may rotate the coma assembly axis angle to find the best angular position. Again, a substantially collimated light source is preferably used as our viewing target for the high order wavefront refraction procedure. Alternatively, a small point source positioned sufficiently far away from the patient can also be used. The importance and the usefulness of using such a target has been discussed in the U.S. application Ser. Nos. 60/773,758 and 11/675,079 which have already been incorporated by reference. It offers sufficient sensitivity for finding a final refraction end point. The end point for the patient to search for is the tightest point image with least amount of star bursts. The star bursts are related and indicative of the existence of higher order aberrations of the vision of the patient.

Some steps of adjusting, back and forth between the amplitude and the angle change are expected. Preferably, the patient has one hand on one knob controlling the amplitude, and the other hand on a knob adjusting the angle. The process can move along quickly, such that these steps will not lead the patient to a state of confusion.

Once the end point for Coma is reached, the wave plate assembly is keyed up for the next Zernike function to be adjusted in a similar manner as is done for the Coma wave plate assembly. Once the end point of that Zernike function is reached, one moves on to the wave plate assembly of the next most significance Zernike function to present to the patient along his/her line of sight at the location as specified, and so forth.

If there is no perceived improvement in the quality of the image when it reaches a certain Zernike on the significance list, at say term number 7, $Z(5,+/-1)$, Secondary Coma, as it is sometimes referred to, in our example shown in the last section, then the wavefront refraction procedure is preferably considered completed.

Even though the feature of being able to continuously vary the amplitude of the wave plate is a significant advantage, we place no limitation on applying all mentioned methods and test techniques to perform a vision improvement test with a series of wave plates having discrete increments in wave amplitude, in place of the continuous variable wave plate device as presented here. Such discrete plates may be mounted on a wheel, e.g., like those in a phoropter, and/or on translational stages to be moved in and out of the line of sight of the patient under test.

Detailed Mechanism for Continuous Adjustability
in Wave Plate Assembly

Figure 2:
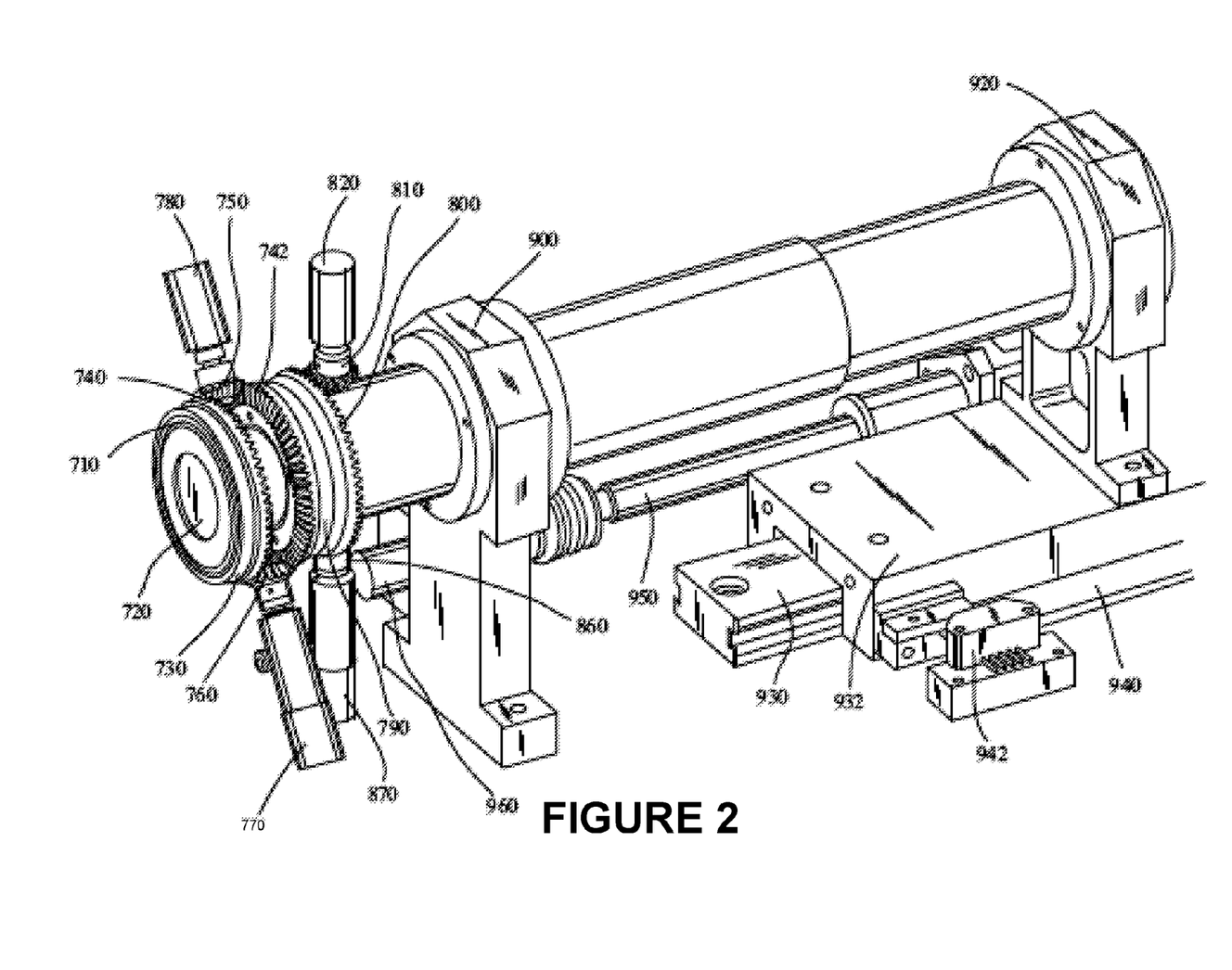
FIG. 2 schematically illustrates an optical instrument in accordance with an embodiment.

In accordance with another embodiment, a motorized mechanism is provided for a Zernike function wave plate assembly, which is applicable to any of the Zernike functions included in this specification. In a preferred embodiment, as illustrated at FIG. 2, a pair of Zernike wave plates are mounted on a rotary ball bearing. One of the wave plate pairs is shown, labeled 720, on bearing 710. Only one of the pair is shown. A view of the second ball bearing and of the second wave plate is blocked in FIG. 2, while the mounting and the motion mechanism is similar to that of the first wave plate. The inner ring of the ball bearing 710 is attached to a bevel gear 740. Similarly, the second wave plate is mounted with a second ball bearing, and the inner portion of the second ball bearing is attached to a second bevel gear 742.

In one embodiment, two pinion gears are used. One pinion gear 760 may be used to drive both bevel gears, as illustrated in FIG. 2, which in turn rotate the pair of wave plates in equal angles but in opposite direction. This counter rotating motion of the Zernike wave plate pair accomplishes the goal of adjusting the amplitude value of the combined wave plate assembly. As it is stated above, and in U.S. application Ser. Nos. 60/773,758 and 11/675,079, when two identical wave plates of a selected Zernike function are substantially aligned with overlapping optical axes, the paired wave plates generate the maximum wavefront amplitude. Using again the Trefoil example, if one uses two wave plates, each with amplitude of 2.5, the maximum amplitude achievable is the sum, or 5. As the relative angle between the wave plate pair increases, the overall amplitude of the assembly unit decreases, and the sum amplitude becomes zero when the optical axis of the two Trefoils are at 90/3, or 30 degrees apart. Therefore, an amplitude control ranges from zero to a maximum of 5. Other desirable adjustable ranges may be constructed similarly utilizing two identical wave plates each having half of a desired maximum.

A motor unit 770 illustrated in FIG. 2 is attached to a drive pinion gear 760. The motor unit 770 can include a DC motor, a step motor, or another suitable mechanism that turns the pinion gear 760. A second pinion gear 750 is also preferably mounted between the two bevel gears 740 and 742. This second pinion gear is used as a rotary angle sensing device and is attached to a rotary encoder 780. Electrical output is fed to an encoder reader which reads pulses and pulse edges. This information is converted to an angular position of the optical axis of each of the wave plates. A second computer program routine then calculates the sum amplitudes of the two wave plates, from the relative angular movement for a given amplitude of the individual wave plates. An overall amplitude of the wave plate pair is then displayed in a monitor, LED, LCD, or any suitable display device, including thermal printer.

Outer rings of ball bearings 730 and a corresponding outer ring for the second ball bearing are attached to inner rings of third and fourth ball bearings. The outer rings of the third and the fourth ball bearings are in turn supported and mounted to the base of the instrument (not shown). The outer ring of the fourth bearing 790 is shown in FIG. 2, but the view of its inner ring is obscured. That inner ring of the fourth ball bearing 790 is attached to a third bevel gear 800. The entire counter rotating unit of the first and second bearings are affixed to the inner ring of the fourth bearing 790, and a second motor 870 is connected to and drives the third pinion gear 860, which in turn rotates the entire counter rotating assembly comprising the first and second ball bearings and the counter rotating wave plates. A second rotary encoder 820 is attached to a fourth pinion gear 810 and senses an angular rotation of the entire counter rotating assembly, which is the angle φ, of the optical axis of the entire counter rotating wave plate pair. Again, the electrical output of the encoder 820 is fed to an encoder reader. A separate computer routine converts electrical pulses from the encoder into an angle reading, which is the angular orientation φ, of the optical axis of the wave plate pair.

Alternate Method of Driving the Continuous Variation in Amplitude and Angle

Instead of using pinion gears to drive the two wave plates of the ACA, which are preferably substantially identical, in opposite direction, preferably at identical angular rates or otherwise in identical angular amounts per increment, one may use synchronized motor drives. In such construction, each wave plate is driven by its own driver electronics. However, two driver circuits are controlled by a closed loop algorithm, such that the two motors still move substantially in "lock-step", or move continuously or jog in steps, in substantially identical angle increments in the same or opposite directions, during any commanded movement. The motor movement is monitored by rotary encoder. An amplitude precision greater than 0.01 diopters is in this way achievable in a 6 diopter astigmatism adjustable wave plate unit.

A Mechanical Design for a Wavefront Refractor

In the previous paragraph, an embodiment was described of a continuously adjustable wave front generation unit of a Zernike function of second order or higher, with non-zero second index (except Z(2, 0). The structure of this may be as described in the U.S. application Ser. Nos. 60/773,758 and 11/675,079. Zernike function wave plates are not made with a symmetric generating machine with two axis grinding and polishing, such as those used to generate sphere and cylindrical surfaces in spectacle lenses. A high precision commercial 4-axis and 5-axis freeform generator machine can cut a surface profile and even polish along the contoured surface. One expects each of such custom-made wave plates would be much more costly. This is an advantage of the technique of certain embodiments which use only two wave plates to create infinite and variable amplitudes and angles, as compared to other embodiments that use a series of wave plates at fixed amplitude, and incremental amplitudes, similar to a series of lenses on a disk inside a phoropter. The former technique also overcomes the problem of requiring a large number of wave plates each with smaller increments in amplitude.

Indeed, FIG. 2 also represents an embodiment of a structural design of the optical layout of a wavefront refractor as described in U.S. application Ser. Nos. 60/773,758 and 11/675,079. That instrument could be manufactured with only two continuously adjustable Zernike functions, i.e., the astigmatism and the defocus. The astigmatism wave plate assembly (300 of FIG. 1) is shown on the left in FIG. 2, and is also referred to as an illustration of how other continuously adjustable wave plate assemblies may be constructed. The defocus assembly (200 in FIG. 1) includes two lenses f1 (210 of FIG. 1) and f2 (220 of FIG. 1), which are mounted in optics holders 910 and 920, respectively. The lens mount 920 is affixed on a linear slide 930, which is movable along the optical axis of the patient's line of sight. A linear encoder strip 940 is attached to the movable platform 932, and an encoder reader head 942, generates electrical pulses as the encoder strip travels across it. The encoder output is fed to a pulse counter, and a computer routine is used to covert the count into the location of lens f2 relative to f1, and it subsequently calculates the diopter power of the defocus assembly unit. The diopter reading is displayed preferably by a suitable method such as was mentioned in the case of the rotary encoder.

The movable platform of the linear slide is driven by a lead screw 950, which is turned by a motor 960. Any kind of motor with the desired speed, resolution and accuracy may be used.

Figure 3:
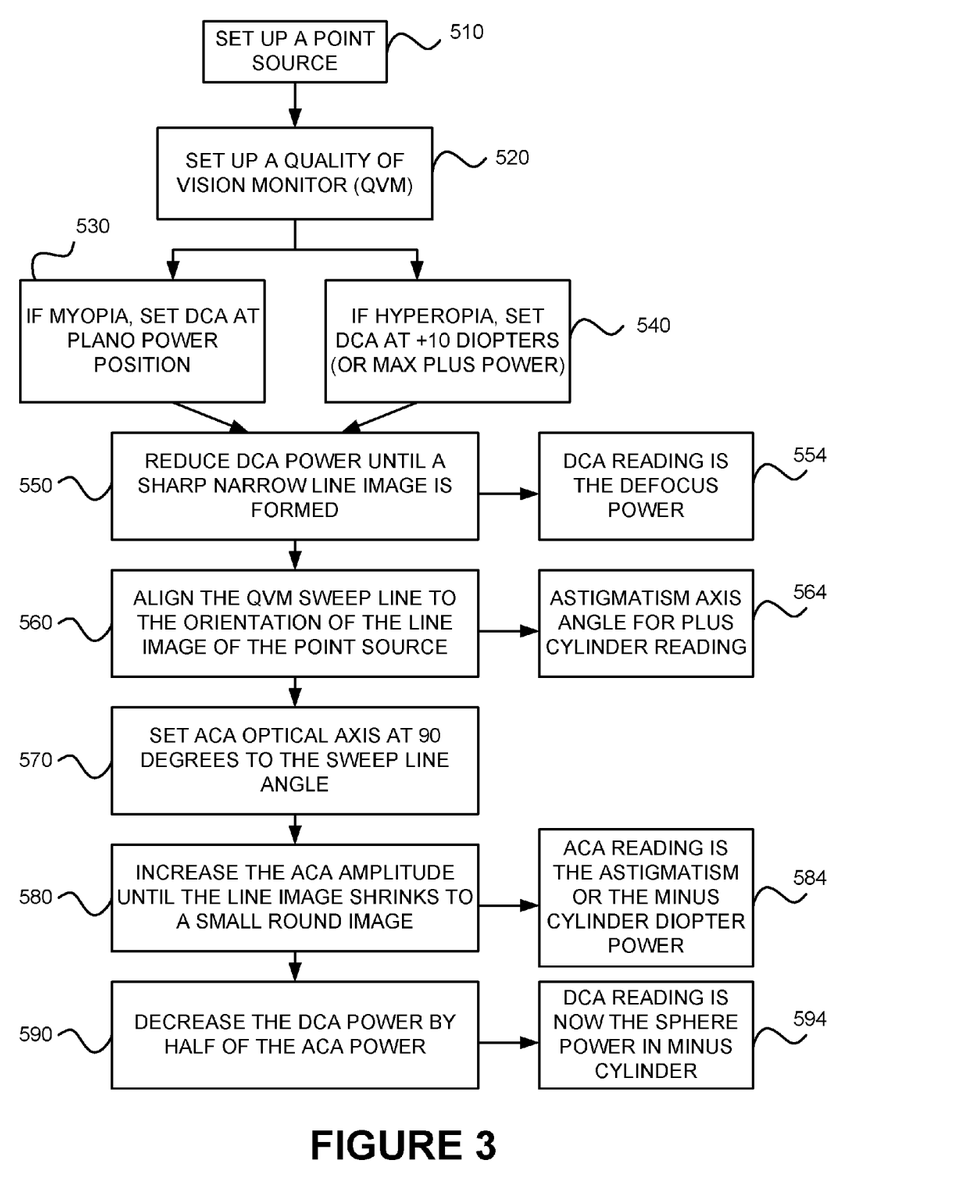
FIG. 3 is a flow chart illustrating a subjective refraction method in accordance with an embodiment.
Figure 4:
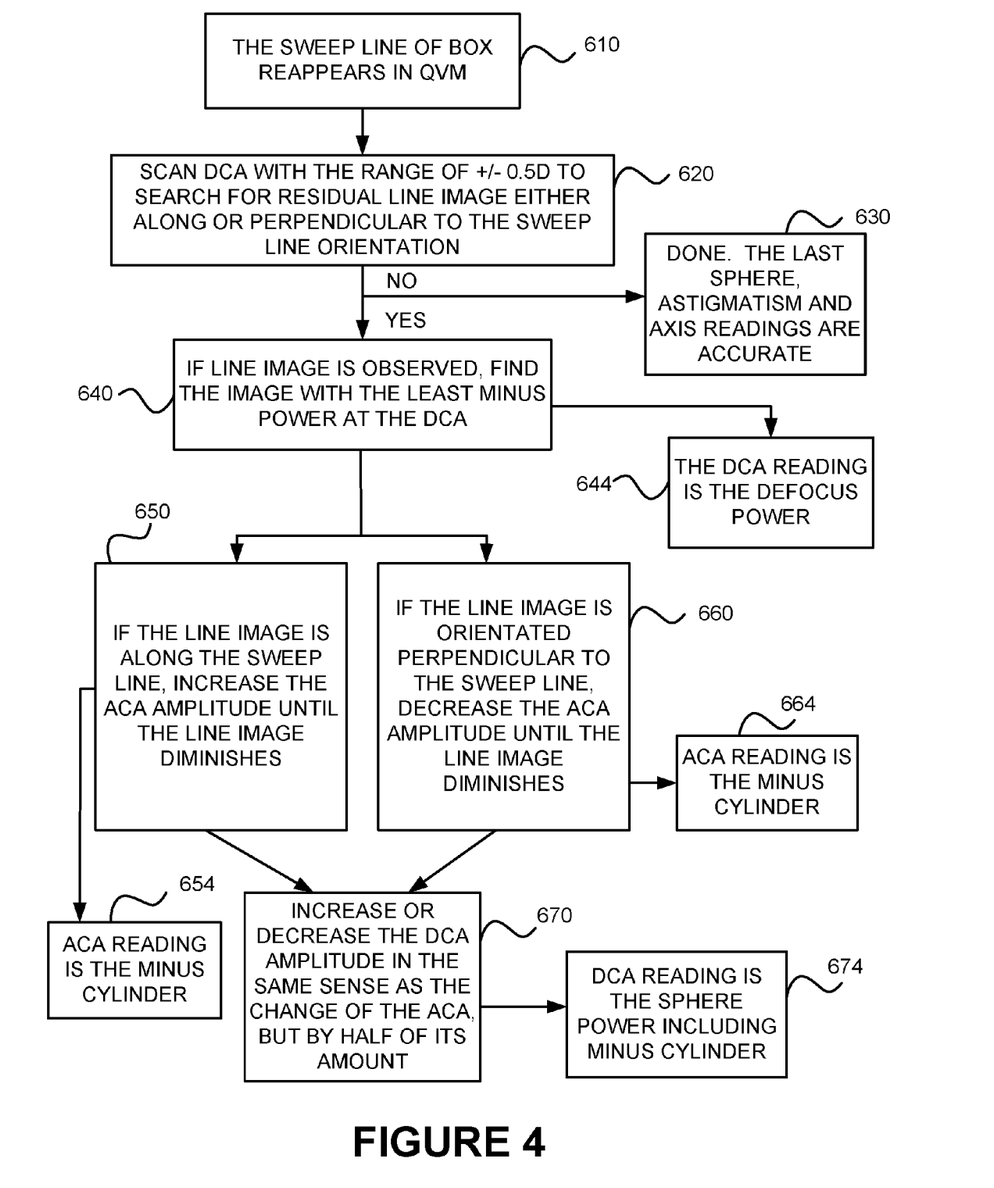
FIG. 4 is a flow chart illustrating a fine tuning of a subjective refraction method in accordance with an embodiment.
Figure 5:
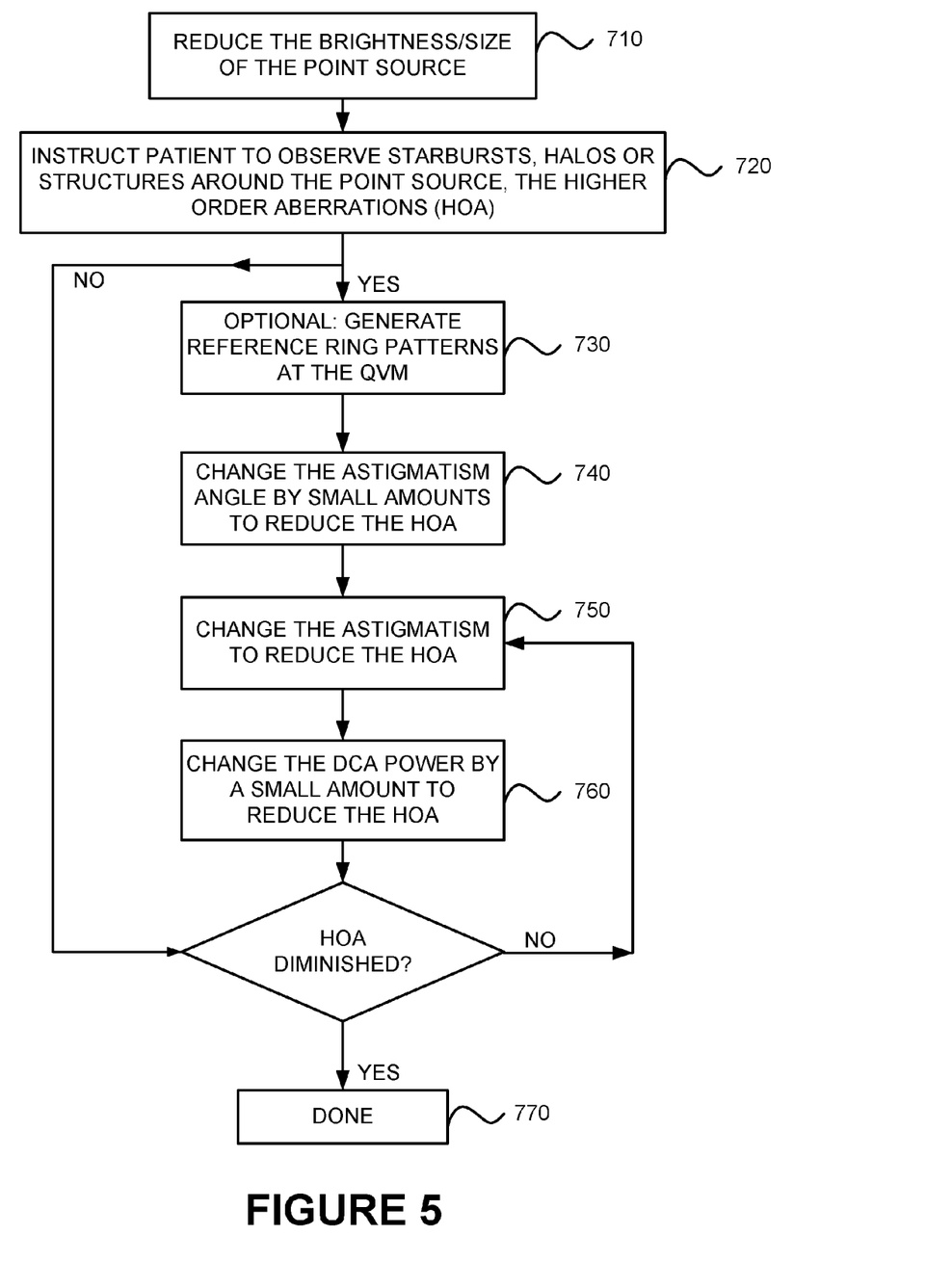
FIG. 5 is a flow chart illustrating correction of high order aberrations in accordance with an embodiment.

FIGS. 3-5 illustrate steps or operations or functions that may be performed in accordance with methods of preferred and alternative embodiments. FIG. 3 illustrates elements 510-594, FIG. 4 illustrates elements 610-674 and FIG. 5 illustrates elements 710-770. These may be performed in different orders and one or more may be skipped in alternative embodiments. These are also non-exhaustive examples, and additional steps, operations or functions may be added or replaced into the technique. Descriptions of these processes are provided in detail in the parent U.S. application Ser. No. 11/675,079, which is incorporated by reference.

Using Alternative Devices to Generate Adjustable Wavefront Profile

While devices and methods have been described in detail for performing subjective wavefront refraction using continuously adjustable wave plates of Zernike functions, the present invention is not limited to a particular type of continuously adjustable wave plates, such as the preferred embodiment that has been described above, namely, an adjustable assembly including two Zernike wave plates of identical, or approximately identical, first index, except that the second index is of opposite sign, $Z(i,+/-j)$, where i and j are the first and the second indices respectively, of the Zernike function. In other embodiments, the continuously adjustable Zernike wavefront profile may be replaced by other wavefront profile generating devices and methods, such as a deformable mirror, a liquid crystal phase plate, or another suitable device that is capable of generating adjustable Zernike wave amplitude and angle. Alternative devices can be much more costly and complicated to operate for a clinical instrument.

The appropriate selected device is preferably placed at a conjugate plane of the patient's pupil or spectacle plane. In the case of using a liquid crystal wave plate, it is placed at the location of the previously described wave plate assembly. In one embodiment, during the refraction process for an optimal wavefront correction, again using the example above and assuming the ordered list is the optimal list, after the second order Zernike function wave plates have been optimized for the patient, the next Zernike function to be optimized is Coma. Again the patient is given two knobs for adjustment control, one to adjust the amplitude and one for the angle. The liquid crystal wave plate generates a Coma in accordance with the input from the control knobs, while the patient is looking at the target, which may be a nearly collimated light source, or other appropriate variation of the target.

So far this alternative process is substantially the same as described previously. Next, moving down the ordered Zernike list, the next step is to optimize the Trefoil. When a Trefoil wavefront profile is requested via signals generated from the patient's turning of knobs, the wavefront profile of the liquid crystal is to be changed to be the sum profile of the Coma amplitude and angle as arrived at from the last optimization for the Coma function. A computer or an appropriate microprocessor is to receive the input from the patient (the knobs in this case, but this is not a limiting factor), and computer routine will preferably perform the sum calculation of (1) the previously arrived at Coma wavefront (amplitude and angle) and (2) the requested Trefoil amplitude and angle. The resulting profile of the sum (Coma and Trefoil) is then sent to the liquid crystal wave plate controller, which generates electrical signals, each of which is to be directed to a specific location of the liquid crystal wave plate, and a two dimensional wavefront profile is then generated. When different signs are received from the knobs, a new Trefoil amplitude or angle is requested. This new Trefoil replaces the last Trefoil, and a new sum wavefront profile (old Coma and new Trefoil) is generated from the computer and is sent to the liquid crystal controller, and so forth, until optimal Trefoil is reached.

The process is then repeated for the next Zernike function down the ordered list. In this example, $Z(4,+/-2)$, or the secondary astigmatism, is to be optimized for the same patient. When that is optimized, the next Zernike function in the ordered list is to be optimized, and so forth, until no improvement is perceived or perceivable by the patient and the optimization process is considered completed.

Alternative Method of Searching for Optimal End Point for Both Adjustable Wave Plates and Alternative Variable Wavefront Profile Generating Devices Such as Liquid Crystal Phase Plate or Deformable Mirrors In another embodiment, a quick and automated method is provided. Instead of providing the test subject with two knobs to control the angle and the amplitude independently, a computer program is used in this case to scan the angle of the wave plate continuously, at a given amplitude value of the Zernike wave plate. For example, an optimized trefoil is to be determined in a test. First, the amplitude of trefoil is set, e.g., at 0.2 microns, and the angle of the optic axis is scanned by the computer quickly. The test subject then presses an input device such as a mouse or a knob, or joystick, or executable display, or voice-activation, to indicate that he or she has seen an improvement point. Repeated scans may be used to check the reliability of the test subject's input for repeatability at or near the same angle or orientation of the wave plate. In one embodiment, if no appreciable improvement is indicated, or an improvement is indicated, the computer increases the amplitude and scans the angle as before. In this embodiment, the test is continued until the test subject presses a second input device indicating the target image quality has become worse rather than improved. Values of the amplitude and the angle at the best vision are noted, e.g., stored in a permanent or removable memory device or printed out on a report, display, or pdf.

Alternatively, if the test subject has confirmed the angle location accurately more than once, the angle orientation of the wave plate may be set at that orientation, and the computer then changes the amplitude, i.e. to increase, or decrease, again in a scanning fashion. The computer monitors the test subject's input to indicate image quality improvement or deterioration. This method substantially increases the test speed, and arrives at the end point of the sharpest image of the target more efficiently.

Figure 6:
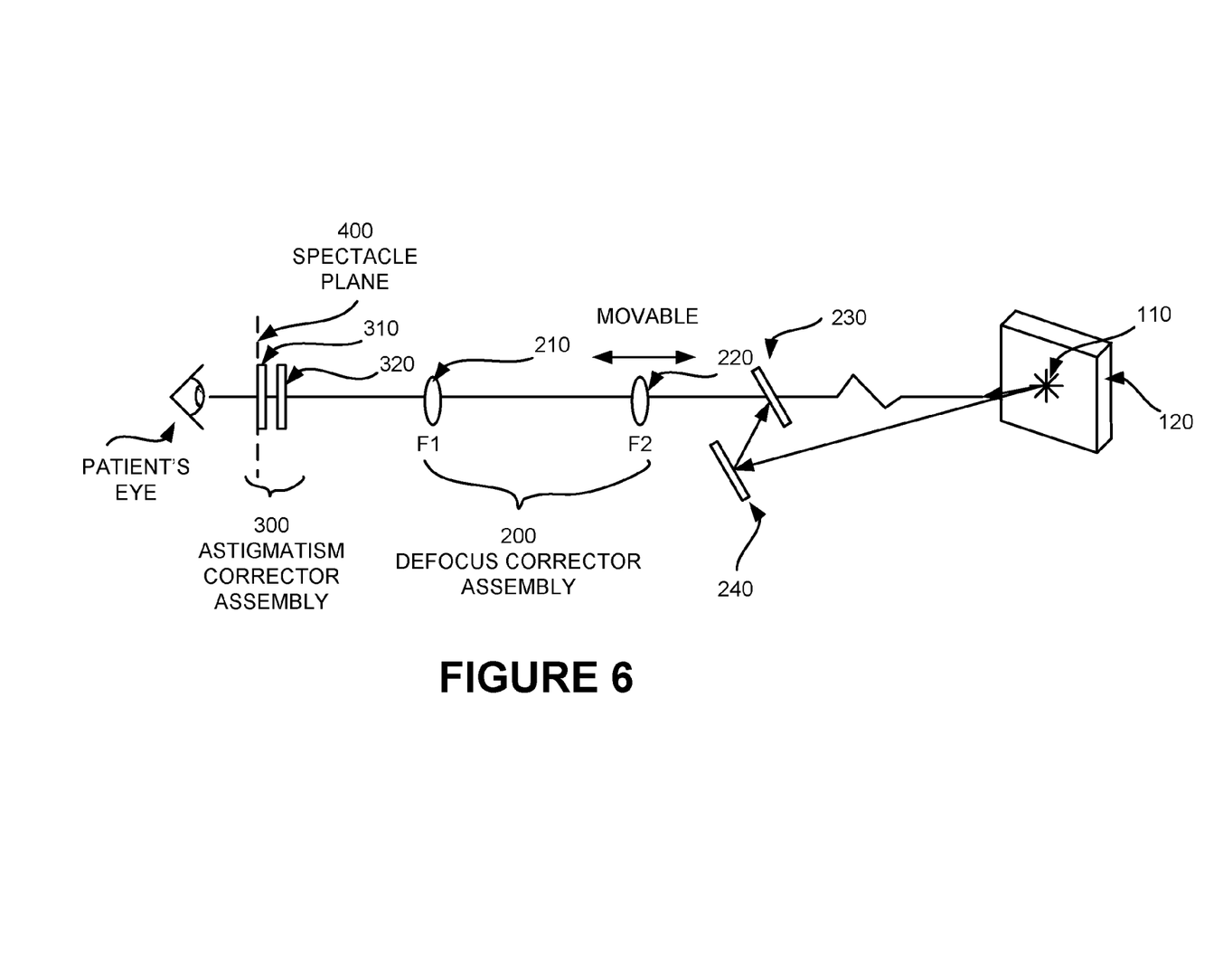
FIG. 6 illustrates a subjective refraction apparatus in accordance with another embodiment.

Referring now to FIG. 6, a deformable mirror 230 or curved reflecting optic 230 may be used, instead of a transmissive assembly such as a liquid crystal wave plate that was indicated as being located at plane 225 in FIG. 1. The wavefront is reflected from the mirror 230, rather than passing through a wave plate or an adjustable Zernike wave plate assembly located at plane 225 in FIG. 1. Reflective optics such as mirrors are to be added in the path of the line of sight of the patient to re-direct the traveling wave from the target to the patient. In FIG. 6, the front surface of a deformable mirror 230 is positioned at the conjugate focal plane of the patient's pupil, similar to the previously described technique. A difference is that a reflective surface of mirror 230 is nearly facing the lens f2, 220 of FIG. 6, or at least rays passing through lens f2 220 encounter reflective optic 230 along the optical path towards target 110. Mirror 230 is also tilted slightly to allow rays traveling along the light path to encounter a plane mirror 240 which is offset from the optical path between lens f2 220 and mirror 230. This offset prevents blocking by mirror 240 of the view between the lens f2 220 and the deformable mirror 230. The plane mirror 240 is also oriented along a path towards the target light source 110. A wavefront refraction technique uses a deformable mirror 230 that preferably serves a substantially same function as using a liquid crystal wave plate 225 (see FIG. 1), except electric signals are sent to actuators that deform the mirror surface to generate the requested shape to generate the optical path difference.

Beneficial Applications

Once an optimized vision of a test subject has been arrived at, a wavefront correction for that person's eye is determined subjectively by the test subject. A correction wavefront profile may be used in a number of vision correction devices or surgery methods. When wavefront correction is used in eyeglasses, contact lenses, or intraocular lenses, the profile correction is typically incorporated by a construction of material thickness profile in such devices. When the wavefront refraction is used in surgical correction methods including PRK, LASIK, LASEK, and intra-corneal surgery, the wavefront correction is achieved by designing a tissue ablation profile either on the cornea or under the corneal flap, or inside the stroma via the use of a femtosecond laser as an example.

The present invention is not limited to the embodiments described above herein, which may be amended or modified without departing from the scope of the present invention as set forth in the appended claims, and structural and functional equivalents thereof.

In methods that may be performed according to preferred embodiments herein and that may have been described above and/or claimed below, the operations have been described in selected typographical sequences. However, the sequences have been selected and so ordered for typographical convenience and are not intended to imply any particular order for performing the operations.

In addition, the subject matter disclosed in all references cited above herein, in addition to the background and summary of the invention sections and including U.S. Pat. Nos. 5,984,916, 6,210,401, 6,325,792, 6,706,036, 6,761,454, 7,114,808, and 7,188,950, are hereby incorporated by reference into the detailed description of the preferred embodiments as disclosing alternative embodiments and components.

I claim:

1. A subjective refraction method for generating a prescription for one or more corrective lenses for a patient, comprising:
   providing at least one point light source outside of the patient's eye as a viewing target;
   forming a blurry image of the point light source at the patient's eye through an optical assembly, the blurry image comprising a refractive error of sphere, astigmatism or higher order aberrations (HOA), or combinations thereof, of the patient's eye;
   adjusting one or more optics of the optical assembly that are continuously disposed along an optical path between the point light source and the patient's eye,
   searching until the patient indicates that the point light source has been focused substantially into a point image; and
   determining a prescription for a corrective lens for the patient's eye based on known parameters of the optical assembly and on at least one adjusted position or orientation, or both, of the one or more optics of the optical assembly.

2. The subjective refraction method of claim 1, wherein the optical assembly comprises a defocus correction assembly or an astigmatism correction assembly, or both.

3. A subjective refraction method for generating a prescription for one or more corrective lenses for a patient, comprising:
   disposing a patient's eye in a substantially fixed position;
   providing at least one point light source outside of the patient's eye as a viewing target;
   forming a blurry image of the point light source at the patient's eye through an optical assembly, the image comprising a refractive error of sphere, astigmatism or higher order aberrations (HOA), or combinations thereof, of the patient's eye;
   adjusting one or more optics of the optical assembly that are continuously disposed along an optical path between the point light source and the patient's eye,
   searching until the patient indicates that the point light source has been focused substantially into a point image; and
   determining a prescription for a corrective lens for the patient's eye based on known parameters of the optical assembly.

4. The subjective refraction method of claim 3, further comprising:
   displaying at least one item in a quality vision marker (QVM) overlapping with or proximate to the point light source, and
   adjusting the at least one display item relative to the point light source.

5. The subjective refraction method of claim 3, wherein the searching comprises adjusting the focusing or astigmatism, or both, of the optical assembly.

6. The subjective refraction method of claim 3, wherein the optical assembly comprises a defocus corrector assembly (DCA) comprising two lenses, and the adjusting comprises adjusting the distance between the two lenses along the optical path until the patient indicates that a blurry image has become focused to a linear image or a point image.

7. The subjective refraction method of claim 6, wherein the optical assembly comprises an astigmatism corrector assembly (ACA) that comprises a pair of astigmatism wave plate lenses.

8. The subjective refraction method of claim 7, further comprising:
   adjusting a defocus power of the DCA within predetermined limits, including searching for a residual linear image of the point light source perpendicular to the sweep line orientation;
   reducing the power of the DCA to attain the least minus power and at which the patient indicates a sharper line image is formed of the point source; and
   decreasing ACA power to reduce a length of the linear image.

9. The subjective refraction method claim 7, comprising adjusting DCA corrective power in incremental spherical powers within a predetermined range and automatically scanning DCA sphere power, until the patient indicates using an input device that the blurry image has become focused to said linear image or said point image.

10. The subjective refraction method of claim 9, comprising:

displaying at least one item in a quality vision marker (QVM) which is overlapping with or proximate to the point light source, and adjusting at least one of the display items relative to said linear image or said point image.

11. The subjective refraction method of claim 7, comprising:

adjusting ACA orientation in incremental angles within a predetermined range and automatically scanning ACA astigmatism angle until the patient indicates using an input device that the orientation of the ACA is aligned with the patient's astigmatism axis.

12. The subjective refraction method of claim 11, comprising adjusting ACA power until the patient indicates using an input device that the linear image has converged into a point image.

13. The subjective refraction method of claim 12, further comprising:

displaying at least one item in a quality vision marker (QVM) overlapping with or proximate to the point light source, and adjusting at least one of the display items relative to the linear image or point image.

14. The subjective refraction method of claim 7, comprising:

adjusting ACA power in incremental astigmatism powers within a predetermined range; and automatically scanning ACA astigmatism power, until the patient indicates using an input device that the image has converged into a point image.

15. The subjective refraction method of claim 14, comprising:

displaying at least one item in a quality vision marker (QVM) which is overlapping with or proximate to the point light source, and adjusting at least one of the display items relative to the linear image or point image.

16. The subjective refraction method of claim 7, further comprising adjusting the prescription for correcting higher order aberrations (HOA) including:

(i) selecting a brightness of the point light source to avoid saturation; or (ii) selecting a physical dimension of the point light source; or (iii) generating points forming a ring pattern or a line pattern, or both, at the QVM; or (iv) searching by the patient for one or more end points including:

(a) adjusting DCA amplitude to converge the blurry image into substantially a line shape; or (b) adjusting ACA amplitude to condense the line shape into a substantially symmetric shape, or (c) both (a) and (b); or (v) combinations of two or more of (i)-(iv).

17. The subjective refraction method of claim 3, wherein the optical assembly comprises a defocus corrector assembly (DCA), and the method comprises inserting one or more lenses of incremental defocus power in the optical path.

18. The subjective refraction method of claim 3, wherein the optical assembly comprises an astigmatism corrector assembly (ACA) that comprises a pair of astigmatism wave plate lenses.

19. The subjective refraction method of claim 18, wherein the adjusting comprises rotating at least one lens of the ACA until the patient indicates that a linear image has become a round or a point image.

20. The subjective refraction method of claim 3, wherein the optical assembly further comprises an astigmatism corrector assembly (ACA), and the method comprises inserting one or more lenses of incremental cylindrical power in the optical path.

21. One or more spectacle, contact or intraocular lenses having a prescription generated by the subjective refraction method of claim 3.

22. The subject refraction method of claim 3, wherein said determining a prescription for a corrective lens for the patient's eye is based at least in part on at least one adjusted position or orientation or both of the one of more optics of the optical assembly.

23. A subjective refraction method for generate a refractive correction prescription for a patient, comprising:

providing at least one point light source outside of a patient's eye and an adjustable optical system for forming an initially blurry image of the point light source at the patient's eye;

while adjusting the optical system, searching until the patient indicates that a blurry image has been focused into a best possible focused point; and adjusting the prescription for correcting higher order aberrations (HOA), including selecting a brightness of the point light source to avoid saturation or selecting the physical dimensions of the point light source, or both.

24. The subjective refraction method of claim 23, wherein the adjusting further comprises:

searching until the patient indicates one or more end points including:

adjusting astigmatism correction amplitude to converge the blurry image in at least one dimension; and adjusting defocus correction amplitude to reduce a long dimension of a substantially linear shape or to converge the substantially linear shape into a best possible symmetric shape, or to a focused point image, or combinations thereof.

* * * * *